United States Patent [19]
Borysko

[11] 3,981,307
[45] Sept. 21, 1976

[54] THERMAL ATTACHMENT OF SURGICAL SUTURES TO NEEDLES

[75] Inventor: Emil Borysko, Somerville, N.J.

[73] Assignee: Ethicon, Inc., Somerville, N.J.

[22] Filed: June 12, 1975

[21] Appl. No.: 586,312

Related U.S. Application Data

[63] Continuation-in-part of Ser. No. 484,471, July 1, 1974, abandoned.

[52] U.S. Cl. .................................. 128/339; 163/1
[51] Int. Cl.² ...................................... A61B 17/06
[58] Field of Search ............. 128/335.5, 339; 163/1

[56] References Cited
UNITED STATES PATENTS

| | | | |
|---|---|---|---|
| 1,665,216 | 4/1928 | Morton et al. | 128/339 |
| 2,014,170 | 9/1935 | Everett | 128/339 |
| 2,928,395 | 3/1960 | Forbes et al. | 128/335.5 |
| 3,799,169 | 3/1974 | Beroff et al. | 128/339 |
| 3,875,946 | 4/1975 | Duncan | 128/339 |

*Primary Examiner*—Dalton L. Truluck
*Attorney, Agent, or Firm*—W. R. Eberhardt

[57] ABSTRACT

A method is provided for anchoring a suture to a needle in which a suture tip is inserted into a recess in the blunt end of a needle and the needle is thereafter heated to expand the suture tip within the recess into tight engagement with the recess walls. Sutures of synthetic polymers attached in this manner are removable from the needle by application of a straight pulling force of less than about 30 ounces.

7 Claims, 3 Drawing Figures

THERMAL ATTACHMENT OF SURGICAL SUTURES TO NEEDLES

CROSS-REFERENCE TO RELATED APPLICATIONS

This application is a continuation-in-part of Ser. No. 484,471, filed July 1, 1974, now abandoned.

BACKGROUND OF THE INVENTION

Surgical sutures are currently attached to needles primarily by inserting one end of the suture into either a channel or a drilled hole in the blunt end of the needle and then mechanically swaging the channel or hole onto the suture so that the latter is held firmly and so that it requires a substantial amount of force to detach the needle from the suture.

This method of attachment suffers from the disadvantage of requiring that the channels or holes be made with great precision, necessitating expensive machinery and skilled labor. A second disadvantage in this method of attachment is that the swaging operation is performed on precision machinery which requires frequent adjustment and replacement of expensive dies by skilled mechanics.

A second method of attaching surgical sutures to needles (used primarily with needles and sutures of small diameter) involves applying a suitable liquid adhesive to the end of the suture before inserting the suture end into a hole in the blunt end of the needle. Proper curing or hardening of the liquid adhesive compound holds the suture firmly in place.

One disadvantage of the adhesive method is that the liquid adhesive compound does not always fill the hole around the suture either because of failure to displace the air in the hole, or because of bubbles in the adhesive. This results in weakened bond strength after curing.

A second disadvantage of the adhesive system of attachment of sutures to needles is that the suture, after insertion into the hole, may be inadvertently dislodged from the hole (either partially or completely) while the needle suture combination is being arranged on a curing tray.

Another disadvantage is that the adhesive compound may not always cure to proper hardness and may thus produce a weakened bond.

Finally, still another disadvantage is that the surfaces of the hole and of the suture tip must be specially prepared to promote adhesion to the adhesive. Such special preparation adds to the cost of providing attachment in this manner.

U.S. Pat. No. 1,558,037, issued to Harry D. Morton on Oct. 20, 1925, discloses a method of attaching a suture to a recess in the blunt end of the needle, which recess is constricted at its neck and enlarged in its interior. The Morton patent discloses filling the excess space around the suture tip with an adhesive material; and alternatively, discloses that some "readily softening suture materials," such as catgut, soften and expand when wet and can thus expand in the presence of water to fill the large portion of the hole. The Morton patent states that such expansion is sufficient to ensure sufficient anchoring of catgut without an adhesive.

The Morton patent discloses that the suture end, upon wetting, expands in diameter and, upon hardening, has a diameter larger than before being wetted. It does not state that the diameter, upon hardening, is as great as it was when wetted, and indeed, it is not because catgut and other collagen materials shrink upon drying, the amount of such shrinking being dependent on the degree of tanning of the collagen. Thus, the suture tip in the Morton method of attachment will, upon drying, be smaller than the enlarged space in the hole and will not be in intimate contact with the surfaces of the hole.

U.S. Pat. No. 1,665,216 issued to Morton et al on Apr. 10, 1928 discloses a method for permanently anchoring catgut suture within a needle recess by utilizing a unique property of catgut, i.e., the ability of catgut to expand into a hard and tough horn-like material upon heating. According to this reference, the expansion of catgut is permanent, the heat appearing to produce a marked change in the structure of the catgut, rendering the same hard, tough and horn-like. The catgut reportedly expands with considerable pressure against the wall of the recess which renders it particularly resistant to attempts to withdraw the suture from the recess. In effect, this reference discloses a method for the permanent attachment of catgut which is an alternative to the mechanical methods of attachment described in the prior art.

The security of attachment of eyeless needles to surgical sutures is prescribed in the U.S. Pharmocopoeia, Vol. XVIII at Page 944. It has been the practice of suture manufactures in the United States and abroad to securely attach the suture to the needle by swaging, with an adhesive, or by other methods so that the minimum pull-out standard recited in the U.S. Pharmacopoeia is met or exceeded.

It has recently been found useful to use needle-suture combinations in which the needle and the suture are readily separable from each other by a sharp tug. Several methods have been devised for preparing needle-suture combinations in which the pull-out values, or the force required for separating the needle from the suture by a straight pull, is within a controlled range, usually less than 30 ounces and preferably between 3 and 26 ounces.

One approach to controlling suture pull-out values is described in co-pending application Ser. No. 516,549, filed Oct. 21, 1974. This approach involves swaging the needle to provide a controlled degree of compression to the end of the suture within the needle recess. This approach is restricted to needle-suture combinations wherein the suture is of large size, i.e., size 4/0 and larger (diameter greater than 7.0 mils), and produces average pull-out values of 3 to 26 ounces, indicating that it takes a straight pull of the magnitude within that range to separate the needle from the suture.

Another approach to the problem is described in U.S. Pat. No. 3,875,946. In this approach sufficient tension is applied to the suture in a swaged needle-suture combination to move the suture relative to the needle recess and the tension is released when the force drops to the range desired for the pull-out value, the range varying for different sizes of suture. This approach is applicable to a broader range of suture sizes than the approach of application Ser. No. 516,549, and is applicable to sizes as small as 8/0.

The present invention provides another method for attaching needles to sutures formed of certain synthetic polymeric materials which provides for the removal of the needle by the application of a controlled amount of pulling force.

SUMMARY OF THE INVENTION

In accordance with the present invention there is provided a method of attaching a suture to a needle having a sharp end and a blunt end which comprises providing an elongated recess at the blunt end of a needle, inserting into said recess one end of a suture made of a normally crystalline, oriented synthetic polymer which becomes substantially disoriented and amorphous and is laterally swellable at an elevated temperature, and thereafter heating said suture end within said recess to a temperature below the melting point of said polymer to expand said suture end to fill the volume of said recess and bring the surface of said suture end into sufficiently tight engagement with the inner surfaces of said recess so that the needle may be removed by a pulling force of less than about 30 ounces.

It is to be noted that, in contrast to the expansion disclosed in the aforementioned Morton 1,558,037 patent, the expansion contemplated in this invention does not involve any take-up of a swelling liquid and is achieved by heat, alone. Heat expansion is substantially irreversible and the suture tip does not contract to any appreciable extent upon cooling and thereby its surfaces remain in tight engagement with the inner surfaces of the recess. Expansion by a swelling liquid, on the other hand, is temporary and is followed by shrinkage as the liquid evaporates, although, as disclosed in the Morton patent, there is not necessarily full shrinkage to the pre-wetted dimensions of the suture tip.

Also in contrast to the Morton et al 1,665,216 patent, the synthetic polymeric suture materials of the present invention are not permanently attached to the needle with the same security obtained by mechanical swaging, but are removable by the application of a pulling force of within the range of about 3 to 26 ounces. Needle suture combinations prepared in accordance with the method of the present invention accordingly possess controlled release properties which are not obtained with the catgut sutures of Morton et al.

Expansion of the thickness of sutures of oriented crystalline polymeric materials is obtained by heating them at a temperature below the melting temperature but above the temperature at which substantially all of their orientation and/or crystallinity disappears. Appropriate temperatures for this change vary with the nature of the material, but a suitable temperature range for a particular material may be readily determined by slowly raising the temperatures of a sample of the material while observing changes in its dimensions and birefringence in a polarizing microscope.

A simple procedure for determining loss of crystallinity in a suture is to observe a sharp change in dimension as its temperature is raised. When a normally crystalline, oriented polymeric suture is heated to the point at which it becomes unoriented and substantially amorphous, it shrinks in length and expands in thickness. When only a short segment of the suture is heated within the recess in a needle, it is the expansion in thickness of the suture at the point where it enters the hole which is most easily visible. For small sutures, expansion at this point is most easily visible with a stereoscopic microscope under a magnification of about 16x.

The sutures suitable for needle attachment by the method of the present invention include monofilaments and braided and covered sutures of a size 4/0 or larger. They may be made of any synthetic polymer which is known to lose substantially all of its orientation and/or crystallinity at a temperature close to but not as high as its melting point. Typical synthetic polymers of this type include nylon, polypropylene, and polyesters, such as polyethylene terephthalate, and homopolymers and copolymers of lactide and glycolide with each other and with other monomers.

The relationships of the transverse dimensions of the suture end and the recess and (in the case of a recess with a constricted portion) between the transverse dimension of the constricted portion of the recess and the enlarged portion of the recess will vary with the nature of the suture material and the amount of transverse expansion which is to be expected from the heating thereof. The neck portion of the recess must have, as a minimum, a somewhat greater transverse dimension than the original transverse dimension of the suture end in order to provide clearance for the insertion of the suture end into the recess. When the neck portion of the recess has a larger transverse dimension than is required for clearance, the maximum possible differential between the enlarged transverse dimension and the constricted transverse dimension, and the maximum possible expansion pressure on the inner walls of the recess, are not utilized and the maximum anchoring effect is not achieved. In some cases this may be desirable and a controlled oversizing of the transverse dimension of the neck portion of the recess (or of the entire recess when the neck is not constricted) may be used to assure a controlled released needle-suture combination in which the suture end may be pulled out of the needle recess by a sharp tug.

In the embodiment of the invention utilizing a recess with a constricted neck, the transverse dimension at the body of the recess is preferably at least 10 percent greater than the transverse dimension of the constricted portion of the recess. The maximum transverse dimension in the enlarged portion of the recess is preferably selected so that the expanded suture end substantially fills the recess and is thus dependent on the nature of the suture material and its expected degree of expansion.

The needle and the suture end therewithin may be heated by any of several procedures. Most simply, the needle may be placed into contact with a hot surface and be heated by conduction. However, other heating techniques, such as induction heating, infra-red heating, resistance heating, or microwave heating may be employed.

Recesses in the blunt end of a needle having a constricted portion of given transverse dimension at a first position and an enlarged portion of greater transverse dimension at a second position farther removed from the blunt end may be of any of a variety of internal shapes and may be made by any of several methods.

The recess may, for example, be bottle-shaped with one enlarged portion and one constricted neck portion. It may also, if desired, have a plurality of annular grooves separated by annular ridges. The recess may be threaded, if desired, the grooves of the threads in this case comprising the enlarged portion of the recess.

One method of forming a bottle-shaped recess is to subject a needle having a cylindrical hole in its blunt end to a round-swaging operation at its blunt end while the hole is empty. Another method is to form a wedge-shaped channel at the blunt end of a needle (with the narrow portion of the wedge closest to the blunt end)

and to then close the channel. It is understood that a needle recess having a constricted neck or other internal restriction designed to increase the pull-out values of the suture are optional designs to be used when pull-out values obtained with a uniform cylindrical recess are below the desired range of 3 to 26 ounces. Such designs may be desirable with certain polymeric materials although in most instances, needles having a straight cylindrical recess provide pull-out values, within the desired range.

BRIEF DESCRIPTION OF THE DRAWINGS

The invention will become more readily apparent upon consideration of the following detailed description when taken in connection with the accompanying drawings wherein.

DETAILED DESCRIPTION

Figure 1:
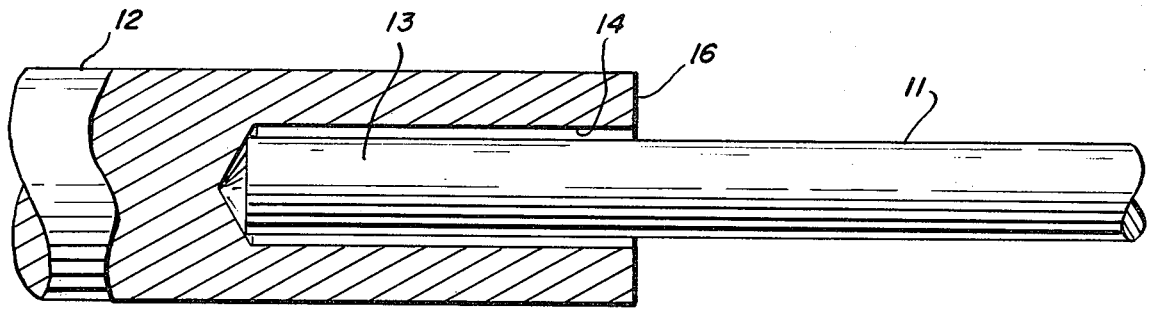
FIG. 1 is an enlarged elevation, partly in cross section of a typical needle-suture junction after the suture end has been inserted into an essentially cylindrical recess in the blunt end of the needle but before the suture end is expanded.

As may be seen from FIG. 1, suture 11 and needle 12 are brought together by inserting suture end 13 into recess 14 in blunt end 16 of the needle. The recess has a transverse dimension slightly greater than that of the suture end to provide a slight clearance for ease of insertion.

Figure 2:
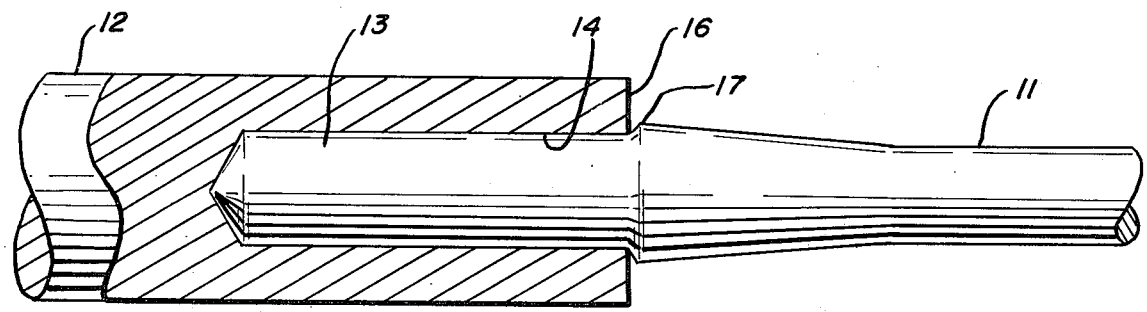
FIG. 2 is an enlarged elevation, partly in cross section, similar to FIG. 1, except that the suture end is shown after expansion to fill the recess.

As may be seen from FIG. 2, suture end 13 expands in width after being heated to substantially fill recess 14. The suture also expands in width in a short segment just outside of recess 14, as shown at 17. The expanded suture tip presses tightly against the inner surfaces of the recess and thereby serves as an anchor to hold the suture and needle together.

Figure 3:
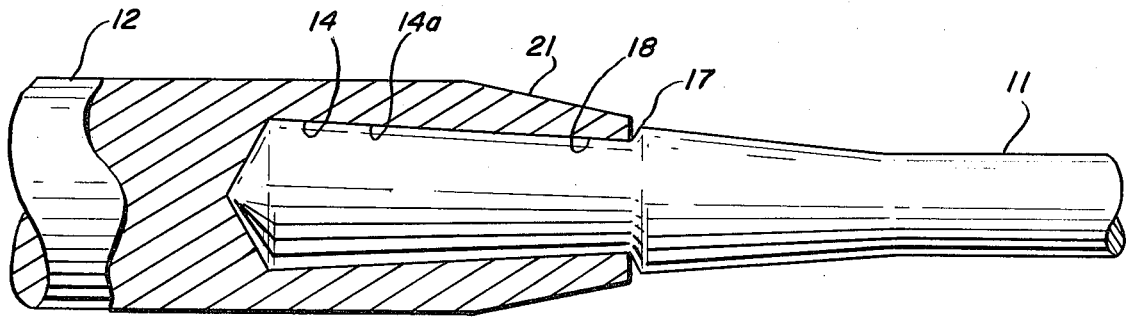
FIG. 3 is an enlarged elevation, partly in cross section, similar to FIG. 2, except that it illustrates an embodiment of the invention in which the recess is constricted at its neck.

In the embodiment of FIG. 3 recess 14a has a constricted neck portion 18 having a transverse dimension slightly greater than the original transverse dimension of the suture end and an enlarged portion 19 farther removed from the blunt end. FIG. 3 also shows a swaged portion 21 at the exterior of the blunt end of the needle, the constriction 18 having been formed by swaging. When the suture end is heated it expands to substantially fill recess 14a and thereby anchors the suture to the needle.

EXAMPLE

A variety of suture materials in sizes 2/0 and 3/0 were attached to drilled needles having cylindrical holes about 16 mils in diameter. The sutures were inserted into the needle recess and heated by contact with a hot surface until the suture expanded at the point of its juncture to the needle, as observed with a stereoscopic microscope at a magnification of 16x. The average pull-out strengths were as follows:

| Suture | Size | Pull-out Strength (ozs.) |
| --- | --- | --- |
| Polypropylene monofilament | 3/0 | 12.9 |
| Polypropylene monofilament | 2/0 | 23.4 |
| Polyethylene terephthalate braid | 2/0 | 22.8 |
| Polyethylene terephthalate braid | 3/0 | 28.6 |
| Nylon monofilament | 2/0 | 13.5 |
| Nylon braid | 2/0 | 16.0 |
| Nylon braid | 3/0 | 6.0 |
| Poly(lactide-co-glycolide) | 3/0 | 22.0 |

What is claimed is:
1. A controlled release needle-suture combination comprising a needle having a sharp end and a blunt end with an elongated recess in said blunt end, and a suture of size 4/0 or larger comprising a normally crystalline, oriented synthetic polymer which becomes substantially disoriented and amorphous and is laterally swellable upon heating to a temperature below the melting point of said polymer, one end of said suture being located within said recess and being swelled therein so that the outer surfaces of said suture end engage the inner surface of said recess to the extent that said suture is removable from said recess by application of a straight pulling force of from about 3 to 30 ounces.

2. A needle-suture combination of claim 1 wherein said suture comprises polypropylene.

3. A needle-suture combination of claim 1 wherein said suture comprises polyethylene terephthalate.

4. A needle-suture combination of claim 1 wherein said suture comprises nylon.

5. A needle-suture combination of claim 1 wherein said suture comprises homopolymers and copolymers of lactide and glycolide.

6. A needle-suture combination of claim 1 wherein said opening in said needle is a drilled hole.

7. A needle-suture combination of claim 1 wherein said suture is size 2/0 or 3/0.

* * * * *